(12) United States Patent
Reinhart et al.

(10) Patent No.: US 7,094,432 B2
(45) Date of Patent: Aug. 22, 2006

(54) COSMETIC COMPOSITIONS CONTAINING ROOIBUS TEA EXTRACT

(75) Inventors: Gale McElroy Reinhart, Middletown, NJ (US); James Joseph Ferone, Bridgewater, NJ (US); Kristen Allison Lattner, Piscataway, NJ (US); Beverly Ann Reisinger, East Brunswick, NJ (US); Christopher James Cashin, Dunellen, NJ (US); Donna Marie Detore, Morris Plains, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 413 days.

(21) Appl. No.: 10/361,294

(22) Filed: Feb. 10, 2003

(65) Prior Publication Data

US 2004/0156798 A1    Aug. 12, 2004

(51) Int. Cl.
*A01N 65/00* (2006.01)
(52) U.S. Cl. .................................................... 424/725
(58) Field of Classification Search ................. 424/725
See application file for complete search history.

(56) References Cited

FOREIGN PATENT DOCUMENTS

| JP | 407155133 | * | 6/1995 |
|----|-----------|---|--------|
| NZ | 9306388   | * | 5/1994 |

* cited by examiner

*Primary Examiner*—Michael Meller
(74) *Attorney, Agent, or Firm*—Julie Blackburn

(57) ABSTRACT

A cosmetic composition comprising Rooibus tea extract in combination with at least one protective agent which is a daytime protective agent, a night time protective agent, or mixtures thereof and methods for exfoliating skin and treating menopausal or peri-menopausal skin.

25 Claims, No Drawings

COSMETIC COMPOSITIONS CONTAINING ROOIBUS TEA EXTRACT

TECHNICAL FIELD

The invention is in the field of compositions for treatment of skin.

BACKGROUND OF THE INVENTION

Treatment of keratinous surfaces such as skin with various types of botanical extracts is well known. As women age, cosmetics companies are becoming more interested in incorporating botanical extracts into skin treatment products because, in many cases, these extracts are believed to contain very minute amounts of ingredients that exert a beneficial effect on the skin. One beneficial effect sought in those who use skin care products is exfoliation. In general, gentle exfoliation of superficial keratinous skin cells results in smooth, clear, luminous skin. While there are a variety of exfoliating ingredients available, such as alpha hydroxy acids, sometimes these acidic ingredients cause skin irritation or dryness. Accordingly, there is a need to find naturally occuring materials that will provide a skin exfoliating effect without causing irritation or dryness. Further, it is desirable to formulate cosmetic products containing such exfoliants with additional ingredients that maximize the effectiveness of the exfoliant and protect the skin from the effects of exfoliation treatment.

There is also a need to provide skin care compositions that are beneficial in treating the adverse effects of menopause and peri-menopause on the skin. Such effects include skin laxity, dryness, yellowing, age spots, wrinkles, lines, and discolorations.

It has been discovered that a particular extract from Rooibus tea is beneficial in exfoliating skin and treating some of the skin conditions associated with menopause or peri-menopause.

It is an object of the invention to provide a method for exfoliating skin with a naturally occurring botanical extract, in particular Rooibus tea.

If is a further object of the invention to provide a method for exfoliating skin and ameliorating the effects of exfoliation on skin by preparing cosmetic compositions containing the exfoliating agent, Rooibus tea extract, in combination with protective agents.

It is a further object to provide a composition for treating the adverse skin conditions associated with menopause and peri-menopause.

It is a further object of the invention to provide cosmetic compositions that contain Rooibus tea extract in combination with protective agents.

It is a further object of the invention to provide a cosmetic composition and method for treating the adverse effects of aging on skin with an extract from Rooibus tea.

SUMMARY OF THE INVENTION

The invention is directed to a cosmetic composition comprising an extract from Rooibus tea in combination with at least one protective agent, which is a daytime protective agent, a night time protective agent, or mixtures thereof.

The invention is also directed to a method for exfoliating the superficial keratin layers of skin comprising applying to the skin a cosmetic composition containing an effective amount of Rooibus tea extract.

The invention further comprises a method for ameliorating the adverse effects of estrogen loss on skin or lips pursuant to menopause or peri-menopause, comprising treating the skin with a composition containing Rooibus tea extract.

DETAILED DESCRIPTION

The term "keratinous surface" means skin, hair, nails, or lips. The term "skin" when used herein means both the facial, neck, and body skin as well as lips. The compositions of the invention may be anhydrous, or in the emulsion form. If the latter, the emulsions may be water-in-oil or oil-in-water. Suitable water-in-oil emulsions contain about 0.1–95%, preferably about 0.5–85%, more preferably about 5–85% by weight of the total composition of water and about 0.1–99%, preferably about 1–90%, more preferably about 3–85% by weight of the total composition of oil. The term "protective agent" means an ingredient or combination of ingredients that maximizes the effectiveness of the Rooibus tea extract on the skin by either promoting better penetration of the extract into the skin, better retaining the extract on the skin, prevent the degradation of the extract on the skin or ameliorating the effects of sunlight and other environmental conditions on skin that is being treated with exfoliating agents.

A. The Rooibus Tea Extract

The Rooibus tea extract used in the claimed method and compositions is preferably obtained from the *Aspalanthus Linearis*, a shrub that is indigenous to South Africa. The Rooibus tea extract may be present ranging from about 0.0001–25%, preferably about 0.0005–20%, more preferably about 0.001–18% by weight of the total composition. Suitable extract is available from a variety of sources including Premier, Inc. The extract may be obtained from all parts of the plant including flowers, leaves, roots, and the like. Particularly preferred is a Rooibus tea extract obtained from leaves of *Aspalanthus Linearis*. The extract may be present in an aqueous solution or suspension containing other ingredients in addition to water, such as glycols, etc. Preferably the Rooibus tea extract is free of caffeine and contains one or more minerals selected from copper, zinc, iron, potassium, calcium, fluoride, manganese, magnesium, or mixtures thereof.

B. The Day Time Protective Agent

The term "day time protective agent" means an agent which enhances the efficacy of the Rooibus tea extract when the composition used by a consumer who is engaging in typical day time activities. The day time protective agent may enhance the efficacy of the Rooibus tea extract by reducing the tendency of the UV rays to degrade the extract components, by interacting chemically with the extract components to provide additional UV activity, by ameliorating the tendency of elements such as wind and rain to reduce the efficacy of the extract on the skin, or otherwise protecting exfoliated skin from being overly prone to sunburn or windburn.

The day time protective agent includes a chemical or physical sunscreen. Suitable day time protective agents include UVA and UVB chemical sunscreens and/or physical sunscreens.

1. UVA Chemical Sunscreens

The day time protective agent preferably comprises at least one UVA sunscreen. The term "UVA sunscreen" means a chemical compound that blocks UV radiation in the wavelength range of about 320 to 400 nm. Preferred UVA sunscreens are dibenzoylmethane compounds having the general formula:

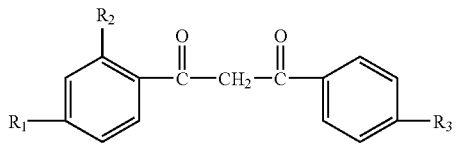

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropyl-benzoylmethane, 4-tert-butyl-4'-methoxydibenzoylmethane, 4,4'-diisopropylbenzoylmethane, 2-methyl-5-isorpoyl-4'-methoxydibenzoymethane, 2-metyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the tradename Eusolex 9020.

The claimed compositions may contain from about 0.001–20%, preferably 0.005–5%, more preferably about 0.005–3% by weight of the composition of UVA sunscreen. In the preferred embodiment of the invention the UVA sunscreen is Avobenzone, and it is present at not greater than about 3% by weight of the total composition.

2. UVB Chemical Sunscreens

The term "UVB sunscreen" means a compound that blocks UV radiation in the wavelength range of from about 290 to 320 nm. A variety of UVB chemical sunscreens exist including α-cyano-β,β-diphenyl acrylic acid esters as set forth in U.S. Pat. No. 3,215,724, which is hereby incorporated by reference in its entirety. Particularly preferred is Octocrylene, which is 2-ethylhexyl 2-cyano-3,3-diphenylacrylate. Preferred is where the composition contains no more than about 10% by weight of the total composition of octocrylene. Suitable amounts range from about 0.001–10% by weight. Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety. Such benzylidene camphor derivatives have the general formula:

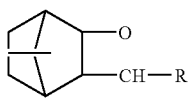

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

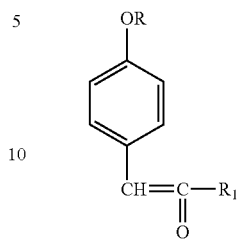

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol MCX, or BASF under the tradename Uvinul MC 80. Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at nor more than about 3% by weight of the total composition.

Also suitable as the UVB screening agents are various benzophenone derivatives having the general formula:

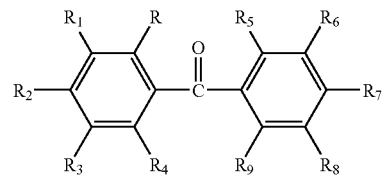

R through $R_9$ are each independently H, OH, $NaO_3S$, SO3H, SO3Na, Cl, R", OR" where R" is C1–20 straight or branched chain alkyl. Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone) and Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

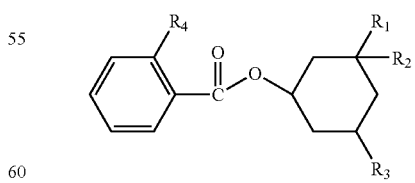

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomenthyl salicylate (also known as homosalate) or menthyl anthranilate. Homosalate is available commercially from Merck under the tradename Eusolex HMS and menthyl anthranilate is commercially available from Haarmann & Reimer under the tradename Heliopan. If present, the Homosalate should be found at no more than about 15% by weight of the total composition.

Various amino benzoic acid derivatives are suitable UVB absorbers including those having the general formula:

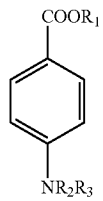

Wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate O), ethyldihydroxypropyl PABA, and the like. If present Padimate O should be found at no more than about 8% by weight of the total composition.

Salicylate derivatives are also acceptable UVB absorbers. Such compounds have the general formula:

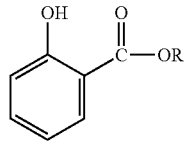

wherein R is a straight or branched chain alkyl, including derivatives of the above compound formed from mono-, di-, or triethanolamines. Particular preferred are octyl salicylate, TEA-salicylcate, DEA-salicylate, and mixtures thereof.

Generally, the amount of the UVB chemical sunscreen present may range from about 0.001–45%, preferably 0.005–40%, more preferably about 0.01–35% by weight of the total composition.

3. Physical Sunscreens

The day time protective agent may also include one or more physical sunscreens. The term "physical sunscreen" means a material that is generally particulate in form that is able to block UV rays by forming an actual physical block on the skin. Examples of particulates that serve as solid physical sunblocks include titanium dioxide, zinc oxide and the like in particle sizes ranging from about 0.001–150 microns.

In general, it is preferred that the claimed compositions contain SPF values ranging from about 1–30, preferably about 2–20, most preferably about 3–18. Calculation of SPF values is well known in the art.

C. The Night Time Protective Agent

Suitable night time protective agents that facilitate efficacy of the Rooibus extract on the skin by either promoting absorption of the extract into the skin by contributing to form a substantive layer of the cosmetic composition containing the extract onto the skin. The substantive layer keeps the active ingredients, including the extract, on the skin surface and facilitates absorption of such actives into the skin or retention of such actives on the skin surface so they can better perform their intended function. Such ingredients may also be referred to as skin penetration enhancers in that they promote penetration of actives into the skin due to the substantive effect they provide on the skin. Examples of such materials include silicone oils, semi-solid or solid waxy materials, triglycerides, esters, paraffinic hydrocarbons, and the like. Preferably the night time protective agent is found in the claimed composition in ranges of from about 0.1–75%, preferably about 0.5–50%, more preferably about 1–40% by weight of the total composition. Such night time protective agents include those further described herein.

1. Silicone Oils

Particularly suitable as the protective agent are various types of silicone oils including water soluble or water insoluble volatile or non-volatile silicone oils. The term "volatile" means that the silicone has a measureable vapor pressure, i.e. a vapor pressure of at least 2 mm. of mercury at 20° C. If volatile, the silicone generally will have a viscosity of about 0.5 to 25 centistokes at 25° C. Suitable volatile silicones include cyclic silicones, linear silicones, or mixtures thereof. Cyclic silicones (or cyclomethicones) are of the general formula:

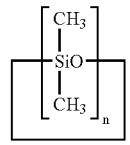

where n=3–6.

Linear volatile silicones in accordance with the invention have the general formula:

where n=0–6, preferably 0–5.

Linear and cyclic volatile silicones are available from various commercial sources including Dow Corning Corporation and General Electric. The Dow Corning volatile silicones are sold under the tradenames Dow Corning 244, 245, 344, and 200 fluids. These fluids comprise octamethylcyclotetrasiloxane, decamethylcyclopentasiloxane, hexamethyldisiloxane, and mixtures thereof.

The silicone may also be nonvolatile, and in particular water insoluble nonvolatile silicones. The term "nonvolatile" means that the silicone has a vapor pressure of less than 2 mm. of mercury at 20° C. A variety of silicones fit this definition including dimethicone, phenyl trimethicone, diphenyl dimethicone, hexadecyl methicone, stearoxydimethicone, stearyl dimethicone, cetyl dimethicone, and so on. Preferred is where the nonvolatile silicone, if present, has a viscosity ranging from about 5–1,000,000 centistokes at 20° C., more preferably about 50–500,000 centistokes at 20° C.

2. Esters

Suitable protective agents also include various types of esters. In general such esters have the formula RCO—OR wherein each R is independently a $C_{1-25}$ straight or branched chain saturated or unsaturated alkyl, alkylcarbonyloxyalkyl, or alkoxycarbonylalkyl, aryl, which may be substituted or unsubstituted with halogen, hydroxyl, alkyl, and the like.

Examples of suitable esters include alkyl acetates, alkyl behenates, alkyl lactates, alkyl benzoates, alkyl octanoates, alkyl salicylates, and in particular $C_{12-15}$ alkyl benzoate. Examples of further esters are set forth on pages 1670–1676 of the CTFA International Cosmetic Ingredient Handbook, Eighth Edition, 2000, which is hereby incorporated by reference.

3. Fats and Oils

Fats and oils are also suitable as protective agents. They may be further defined as glyceryl esters of fatty acids (triglycerides), as well as the synthetically prepared esters of glycerin and fatty acids having the following general formula:

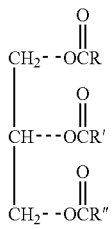

wherein R, R', and R" are each independently fatty acid radicals. Examples of such materials include oils such as apricot kernel oil, avocado oil, canola oil, olive oil, sesame oil, peanut oil, soybean oil, trilinolenin, trilinolein, trioctanoin, tristearin, triolein, sesame oil, rapeseed oil, sunflower seed oil, and so on.

4. Fatty Acids

Fatty acids may also serve as protective agents. Fatty acids are the carboxylic acids obtained by hydrolysis of animal or vegetable fats and oils. Carboxylic acids having alkyl chains shorter than about seven carbon atoms are not generally considered fatty acids. Fatty acids have the general structure R—COOH where R is a straight or branched chain saturated or unsaturated $C_{7-65}$ alkyl. Examples of suitable fatty acids include arachidic acid, arachidonic acid, behenic acid, capric acid, caproic acid, caprylic acid, coconut acid, corn acid, cottonseed acid, hydrogenated coconut acid, hydroxystearic acid, lauric acid, linoleic acid, linolenic acid, linseed acid, myristic acid, oleic acid, palmitic acid, palm kernel acid, soy acid, tallow acid, and the like.

5. Fatty Alcohols

Suitable fatty alcohols include those made by reducing the fatty acid —COOH group to the hydroxyl function. They generally have the formula $RCH_2OH$. Examples of fatty alcohols are behenyl alcohol, $C_{9-11}$ alcohol, $C_{12-13}$ alcohol, $C_{12-15}$ alcohol, $C_{12-16}$ alcohol, caprylic alcohol, cetearyl alcohol, cetyl alcohol, coconut alcohol, decyl alcohol, lauryl alcohol, myristyl alcohol, oleyl alcohol, and the like.

6. Hydrocarbons

Hydrocarbons also serve as good skin penetrants for use as the night time protective agent. Hydrocarbons are generally chemically inert. Examples of suitable hydrocarbons include $C_{7-60}$ isoparaffins, ethane, heptane, hexane, hydrogenated polyisobutene, isobutane, isododecane, isoeicosane, isohexadecane, isopentane, microcrystalline wax, mineral oil, mineral spirits, paraffin, petrolatum, petroleum distillates, squalene, polyethylene, and mixtures thereof. Preferred hydrocarbons are mineral oil and polyethylene.

Preferred is where the night time protective agents are silicone oil, fatty alcohols, esters, fatty acids, and mixtures thereof.

D. Other Ingredients

The claimed composition may contain other ingredients in addition to the Rooibus tea extract, day time protective agent, and night time protective agents. Such ingredients include other botanical extracts, humectants, preservatives, polymers, particulates, surfactants, and the like.

1. Organic Surfactants

Preferably, the claimed compositions contain one or more surfactants including those having anionic, nonionic, amphoteric, zwitterionic, or cationic moieties. The organic surfactant, if present, should range from about 0.001–30%, preferably about 0.005–25%, preferably about 0.01–20% by weight of the total composition. The compositions of the invention preferably comprise about 0.01–20%, preferably about 0.1–15%, more preferably about 0.5–10% by weight of the total composition of a surfactant. Particularly preferred are one or more nonionic surfactants or emulsifiers including alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Beheneth 5–30, which is formed by the reaction of behenyl alcohol and ethylene oxide where the number of repeated ethylene oxide units is 5 to 30; Ceteareth 2–100, formed by the reaction of a mixture of cetyl and stearyl alcohol with ethylene oxide, where the number of repeating ethylene oxide units in the molecule is 2 to 100; Ceteth 1–45 which is formed by the reaction of cetyl alcohol and ethylene oxide, and the number of repeating ethylene oxide units is 1 to 45, and so on. Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol.

Also suitable as the nonionic surfactant are alkyoxylated carboxylic acids, which are formed by the reaction of a carboxylic acid with an alkylene oxide or with a polymeric ether. The resulting products have the general formula:

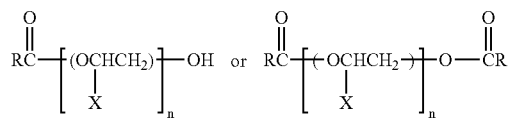

where RCO is the carboxylic ester radical, X is hydrogen or lower alkyl, and n is the number of polymerized alkoxy groups. In the case of the diesters, the two RCO— groups do not need to be identical. Preferably, R is a $C_{6-30}$ straight or branched chain, saturated or unsaturated alkyl, and n is from 1–100.

Also suitable as the nonionic surfactant are monomeric, homopolymeric and block copolymeric ethers. Such ethers are formed by the polymerization of monomeric alkylene oxides, generally ethylene or propylene oxide. Such polymeric ethers have the following general formula:

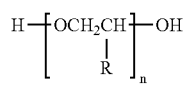

wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20–85, sorbitan oleate, sorbitan palmitate, sorbitan sesquiisostearate, sorbitan stearate, and so on.

Also suitable as nonionic surfactants are silicone surfactants, which are defined as silicone polymers which have at least one hydrophilic radical and at least one lipophilic radical. The silicone surfactants may be a liquid or solid at room temperature and are generally of the water-in-oil or oil-in-water type. Preferably, they have an Hydrophile/Lipophile Balance (HLB) of 2 to 18. Preferably the organosiloxane is a nonionic surfactant having an HLB of 2 to 12, preferably 2 to 10, most preferably 4 to 6. The HLB of a nonionic surfactant is the balance between the hydrophilic and lipophilic portions of the surfactant and is calculated according to the following formula:

$$HLB = 7 + 11.7 \times \log M_w/M_o$$

where $M_w$ is the molecular weight of the hydrophilic group portion and $M_o$ is the molecular weight of the lipophilic group portion.

The term "organosiloxane polymer" means a polymer containing a polymeric backbone including repeating siloxy units that may have cylic, linear or branched repeating units, e.g. di(lower)alkylsiloxy units, preferably dimethylsiloxy units. The hydrophilic portion of the organosiloxane is generally achieved by substitution onto the polymeric backbone of a radical that confers hydrophilic properties to a portion of the molecule. The hydrophilic radical may be substituted on a terminus of the polymeric organosiloxane, or on any one or more repeating units of the polymer. In general, the repeating dimethylsiloxy units of modified polydimethylsiloxane emulsifiers are lipophilic in nature due to the methyl groups, and confer lipophilicity to the molecule. In addition, longer chain alkyl radicals, hydroxypolypropyleneoxy radicals, or other types of lipophilic radicals may be substituted onto the siloxy backbone to confer further lipophilicity and organocompatibility. If the lipophilic portion of the molecule is due in whole or part to a specific radical, this lipophilic radical may be substituted on a terminus of the organosilicone polymer, or on any one or more repeating units of the polymer. It should also be understood that the organosiloxane polymer in accordance with the invention should have at least one hydrophilic portion and one lipophilic portion.

The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof.

The term "lipophilic radical" means an organic radical that, when substituted onto the organosiloxane polymer backbone, confers lipophilic properties to the substituted portion of the polymer. Examples of organic radicals which will conver lipophilicity are $C_{1-40}$ straight or branched chain alkyl, fluoro, aryl, aryloxy, $C_{1-40}$ hydrocarbyl acyl, hydroxypolypropyleneoxy, or mixtures thereof. The $C_{1-40}$ alkyl may be non-interrupted, or interruped by one or more oxygen atoms, a benzene ring, amides, esters, or other functional groups.

The polymeric organosiloxane surfactant used in the invention may have any of the following general formulas:

$$M_xQ_y, \text{ or}$$

$$M_xT_y, \text{ or}$$

$$MD_xD'_yD''_zM$$

wherein each M is independently a substituted or unsubstituted trimethylsiloxy endcap unit. If substituted, one or more of the hydrogens on the endcap methyl groups are substituted, or one or more methyl groups are substituted with a substituent that is a lipophilic radical, a hydrophilic radical, or mixtures thereof. T is a trifunctional siloxy unit having the empirical formula $RR'SiO_{1.5}$ or $RRSiO_{1.5}$. Q is a quadrifunctional siloxy unit having the empirical formula $SiO_2$, and D, D', D", x, y, and z are as set forth below, with the proviso that the compound contains at least one hydrophilic radical and at least one lipophilic radical. Preferred is a linear silicone of the formula:

$$MD_xD'_yD''_zM$$

wherein $M = RRRSiO_{1/2}$

D and $D' = RR'SiO_{2/2}$ $D'' = RRSiO_{2/2}$ x, y, and z are each independently 0–1000, where R is methyl or hydrogen, and R' is a hydrophilic radical or a lipophilic radical, with the proviso that the compound contains at least one hydrophilic radical and at least one lipophilic radical.

Most preferred is wherein
M trimethylsiloxy
$D = Si[(CH_3)][(CH_2)_nCH_3]O_{2/2}$ where n=0–40,
$D' = Si[(CH_3)][(CH_2)_o\!-\!O\!-\!PE)]O_{2/2}$ where PE is $(-C_2H_4O)_a(-C_3H_6O)_bH$, o=0–40,
a=1–100 and b=1–100, and More specifically, suitable silicone sulfactants have the formula:

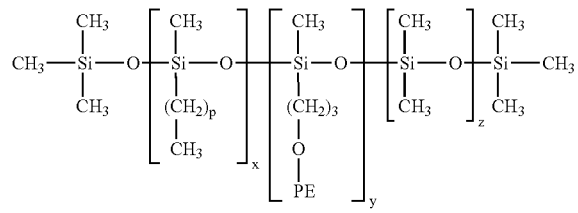

wherein p is 0–40, and
PE is $(-C_2H_4O)_a(-C_3H_6O)_b-H$ where x, y, z, a, and b are such that the maximum molecular weight of the polymer is approximately about 50,000.

Another type of preferred organosiloxane emulsifier suitable for use in the compositions of the invention are emulsifiers sold by Union Carbide under the Silwet™ trademark. These emulsifiers are represented by the following generic formulas:

$$(Me_3Si)_{y-2}[(OSiMe_2)_{x/y}O\!-\!PE]_y$$

wherein PE=—(EO)$_m$(PO)$_n$R
R=lower alkyl or hydrogen
Me=methyl
EO is polyethyleneoxy
PO is polypropyleneoxy
m and n are each independently 1–5000
x and y are each independently 0–5000, and

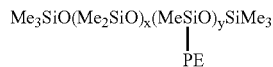

wherein PE=—CH$_2$CH$_2$CH$_2$O(EO)$_m$(PO)$_n$Z
Z=lower alkyl or hydrogen, and
Me, m, n, x, y, EO and PO are as described above, with the proviso that the molecule contains a lipophilic portion and a hydrophilic portion.

Also suitable as nonionic silicone surfactants are hydroxy-substituted silicones such as dimethiconol, which is defined as a dimethyl silicone substituted with terminal hydroxy groups.

Examples of silicone surfactants are those sold by Dow Coming under the tradename Dow Corning 3225C Formulation Aid, Dow Coming 190 Surfactant, Dow Coming 193 Surfactant, Dow Coming Q2-5200, and the like are also suitable. In addition, surfactants sold under the tradename Silwet by Union Carbide, and surfactants sold by Troy Corporation under the Troysol tradename, those sold by Taiwan Surfactant Co. under the tradename Ablusoft, those sold by Hoechst under the tradename Arkophob, are also suitable for use in the invention.

Suitable cationic, anionic, zwitterionic, and amphoteric surfactants are disclosed in U.S. Pat. No. 5,534,265, which is hereby incorporated by reference in its entirety.

2. Humectants

Preferably the compositions of the invention comprise 0.01–30%, preferably 0.5–25%, more preferably 1–20% by weight of the total composition of one or more humectants. Suitable humectants include materials such as glycols, sugars, and the like. Suitable glycols include polyethylene and polypropylene glycols such as PEG 4-240, which are polyethylene glycols having from 4 to 240 repeating ethylene oxide units; as well as C$_{1-6}$ alkylene glycols such as propylene glycol, butylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Preferably, the humectants used in the composition of the invention are C$_{1-6}$, preferably C$_{2-4}$ alkylene glycols, most particularly butylene glycol.

3. Other Botanical Extracts

It may be desirable to include one or more additional botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including acacia (dealbata, farnesiana, senegal), acer saccharinum (sugar maple), acidopholus, acorus, aesculus, agaricus, agave, agrimonia, algae, aloe, citrus, brassica, cinnamon, orange, apple, blueberry, cranberry, peach, pear, lemon, lime, pea, seaweed, green tea, chamomile, willowbark, mulberry, poppy, and those set forth on pages 1646 through 1660 of the *CTFA Cosmetic Ingredient Handbook,* Eighth Edition, Volume 2. Preferred are botanical extracts including *Glycyrrhiza Glabra, Salix Nigra, Diooscorea Villosa, Macrocycstis Pyrifera, Pyrus Malus, Saxifraga Sarmentosa, Vitis Vinifera, Morus Nigra, Scutellaria Baicalensis, Anthemis Nobilis, Salvia Sclarea, Rosmarinus Officianalis,* Citrus *Medica Limonum,* and mixtures thereof.

4. Gellants

It may be desireable to include other gellants in the oil or water phase of the composition to provide gelling. Such gellants may be included a range of about 0.1–20%, preferably about 1–18%, more preferably about 2–10% by weight of the total composition is suggested. Suitable gellants include soaps, i.e. salts of water insoluble fatty acids with various bases. Examples of soaps include the aluminum, calcium, magnesium, potassium, sodium, or zinc salts of C$_{6-30}$, preferably C$_{10-22}$ fatty acids.

Also suitable are hydrocolloids such as gellan gum, gum arabic, carrageenan, and those set forth in U.S. Pat. No. 6,197,319 which is hereby incorporated by reference in its entirety.

Water soluble synthetic polymeric materials are also good gellants, including polymers of acrylic acid or C$_{1-20}$ esters thereof, which may be crosslinked or uncrosslinked. Examples include Carbopol (polymer of acrylic acid crosslinked with a polyfunctional agent which is the allyl ether of sucrose or the allyl ether of pentaerythritol), and the like.

5. Preservatives

The composition may contain 0.001–8%, preferably 0.01–6%, more preferably 0.05–5% by weight of the total composition of preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, calcium benzoate, calcium propionate, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and all of those disclosed on pages 570 to 571 of the CTFA Cosmetic Ingredient Handbook, Second Edition, 1992, which is hereby incorporated by reference.

6. Particulates

It may be desirable to incorporate one or more particulate materials such as pigments, powders, and the like into the claimed composition to provide various effects. For example, inclusion of small amounts of powders will improve consistency of the composition and may provide a more aesthetic color. If desired, small amounts of pigments may also be included, particularly in the event where it is desired to provide color to the skin. If present the particulates range from about 0.001–20%, more preferably about 0.01–18% of particulate matter having a particle size of 0.01 to 200, preferably 0.25–100 microns. The particulate matter may be colored or non-colored (for example white) non-pigmentitious powders. Suitable non-pigmentatious powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

The particulate matter component also may comprise various organic and/or inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof The claimed compositions provide an excellent vehicle for the Rooibus tea extract, and enhance the efficacy and other beneficial properties of the extract on the skin.

The invention will be further described in connection with the following examples which are set forth for the purposes of illustration only.

EXAMPLE 1

An emulsion cream was prepared as follows:

| INGREDIENT | w/w % |
|---|---|
| Petrolatum | 3.50 |
| Squalane | 2.10 |
| Lauryl lactate | 1.50 |
| Cetearyl ethylhexanoate | 4.31 |
| Propyl paraben | 0.10 |
| Ethylhexyl hydroxystearate | 0.10 |
| Ethyl paraben | 0.05 |
| Jojoba seed oil | 0.10 |
| White Birch extract | 0.01 |
| Phenoxyethanol | 0.70 |
| Tocopheryl acetate | 0.20 |
| *Aloe barbadensis* extract | 0.05 |
| Retinyl palmitate | 0.001 |
| Kinetin | 0.08 |
| Cyclomethicone/dimethicone copolyol | 15.00 |
| Cyclomethicone/dimethiconol | 4.00 |
| Cyclomethicone | 8.35 |
| Quaternium-18 hectorite | 2.00 |
| Clary extract/galbanum gum extract, chamomileflower extract, green tea extract, phenoxyethanol/rosemary leaf extract | 0.10 |
| Titanium dioxide/caprylic capric triglycerides/mineral oil/alumina/polyhydroxtearic acid/silica | 1.00 |
| Sodium chloride | 1.50 |
| Magnesium ascorbyl phosphate | 0.10 |
| Glycerin | 4.00 |
| Butylene glycol | 2.00 |
| PEG-4 | 3.00 |
| Methyl paraben | 0.20 |
| Panthenol | 0.10 |
| Aspartic acid/glutamic acid/alanine/dextrin/urea/sucrose/fructose/glucose/hexylene glycol | 0.50 |
| Glucose/sorbitol/citric acid | 3.00 |
| Meadowsweet extract | 1.00 |
| Water/saccharomyces zinc ferment/saccharomyces copper ferment/saccharomyces manganese ferment/saccharomyces iron ferment/saccharomyces silicon ferment/saccharomyces potassium ferment | 0.01 |
| Water/butylene glycol/*Aspalanthus Linearsis* leaf extract | 0.05 |

-continued

| INGREDIENT | w/w % |
|---|---|
| *Phyllanthus Emblica* fruit extract | 0.01 |
| Methoxypropylgluconamide/water | 0.50 |
| Rooibus Tea Extract | 0.10 |
| Water | QS |

The composition was prepared by heating water, glycols, preservatives, magnesium ascorbyl phosphate, silica, glycerin and talc to 80° C. with sweep mixing. Once uniform, the carbomer solution was added with sweep agitation maintaining a temperature of 80° C. In a separate vessel oil phase ingredients (Octyl methoxycinnamate to Sorbitan stearate) were mixed with propeller agitation and heated to 80° C. Once both phases reached 80° C. the oil phase was transferred into the water phase with fast agitation. Once the transfer was completed the composition was neutralized with triethanolamine, followed by addition of the mica and titanium dioxide. The mixture was homogenized for 15 minutes, then cooled to 50° C. with continuous agitation. Once the bulk was cooled to 50° C. the remaining ingredients were added with mixing. The sodium hydroxide and kinetin were premixed with water (1%) in a container before adding to the mixture. The mixture was then cooled to 30° C. and poured into suitable containers.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A cosmetic composition comprising Rooibus tea (Aspalanthus Linearis) extract in combination with at least one silicone or at least one ester agent which is a daytime protective agent, a night time protective agent, or mixtures thereof.

2. The composition of claim 1 wherein the composition is an emulsion form.

3. The composition of claim 2 wherein the emulsion is an oil-in-water emulsion.

4. The composition of claim 2 wherein the emulsion is a water-in-oil emulsion.

5. The composition of claim 1 futher comprising a chemical sunscreen, a physical sunscreen, or mixtures thereof.

6. The composition of claim 5 wherein the chemical sunscreen is a UVA sunscreen, a UVB sunscreen, or mixtures thereof.

7. The composition of claim 6 wherein the chemical sunscreen is a mixture of UVA and UVB sunscreens.

8. The composition of claim 5 wherein the chemical sunscreen is a mixture of UVA and UVB sunscreens and the composition has an SPF of at least about 4.

9. The composition of claim 7 wherein the UVA sunscreen is dibenzoyl methane compound.

10. The composition of claim 7 wherein the UVB sunscreen is an a -cyano-β,β-diphenyl diphenyl acrylic acid ester, a benzylidene camphor compound, a cinnamate compound, a benzophenone compound, a menthyl salicylate compound, a benzoic acid derivative, a salicylate compound, or mixtures thereof.

11. The composition of claim 10 wherein the UVB sunscreen is Cinoxate, Homosalate, methyl anthranilate, Octocrylene, octyl methoxycinnamate, octyl salicylate, Oxybenzone, Padimate O, phenylbenzimidazole sulfonic acid, Sulisobenzone, TEA-salicylate, and mixtures thereof.

12. The composition of claim 5 wherein the physical sunscreen is titanium dioxide, zinc oxide, or mixtures thereof.

13. The composition of claim 9 wherein the dibenzoylmethane compound is Avobenzone, and it is present at no more than about 3% by weight of the total composition.

14. The composition of claim 11 wherein the Cinoxate is present at no more than about 3% by weight of the total composition.

15. The composition of claim 10 Homosalate is present at no more than about 15% by weight of the total composition.

16. The composition of claim 10 wherein the octocrylene is present at no more than about 10% by weight of the composition.

17. The composition of claim 10 wherein the padimate O is present at no more than about 8% by weight of the total composition.

18. The composition of claim 9 wherein the UVA sunscreen is Avobenzone.

19. The composition of claim 18 wherein the UVB sunscreen is cinoxate, Homosalate, Octocrylene, octyl methoxycinnamate, octyl salicylate, Oxybenzone, Padimate O, or mixtures thereof.

20. The composition of claim 19 additionally containing one or more plant extracts selected from the group consisting of *Glycyrrhiza Glabra, Salix Nigra, Diooscorea Villosa, Macrocycstis Pyrifera, Pyrus Malus, Saxifraga Sarmentosa, Vitis Vinifera, Morus Nigra, Scutellaria Baicalensis, Anthemis Nobilis, Salvia Sclarea, Rosmarinus Officianalis, Citrus Medica Limonum,* and mixtures thereof.

21. The composition of claim 1 further comprising a fatty alcohol, fatty acid, hydrocarbon, or mixtures thereof.

22. The composition of claim 21 wherein the silicone is silicone oil comprising a cyclomethicone, dimethicone, phenyl trimethicone, or mixtures thereof.

23. The composition of claim 1 further comprising one or more humectants.

24. The composition of claim 1 further comprising one or more thickening agents.

25. The composition of claim 1 further comprising one or more nonionic surfactants.

* * * * *